(12) United States Patent
Arima et al.

(10) Patent No.: US 9,981,819 B2
(45) Date of Patent: May 29, 2018

(54) SHEET CONVEYANCE APPARATUS THAT DETECTS OVERLAPPING OF PLURALITY OF SHEETS, AND IMAGE READING APPARATUS

(71) Applicant: CANON KABUSHIKI KAISHA, Tokyo (JP)

(72) Inventors: Makoto Arima, Abiko (JP); Taishi Tomii, Matsudo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days. days.

(21) Appl. No.: 15/228,110

(22) Filed: Aug. 4, 2016

(65) Prior Publication Data

US 2017/0057768 A1 Mar. 2, 2017

(30) Foreign Application Priority Data

Aug. 27, 2015 (JP) ................ 2015-168139

(51) Int. Cl.
| | |
|---|---|
| *B65H 3/06* | (2006.01) |
| *B65H 7/12* | (2006.01) |
| *B65H 5/06* | (2006.01) |
| *G01N 29/07* | (2006.01) |
| *G01N 29/11* | (2006.01) |
| *G01N 29/34* | (2006.01) |
| *G01N 29/44* | (2006.01) |

(52) U.S. Cl.
CPC ............... *B65H 7/125* (2013.01); *B65H 3/06* (2013.01); *B65H 5/062* (2013.01); *G01N 29/07* (2013.01); *G01N 29/11* (2013.01); *G01N 29/343* (2013.01); *G01N 29/4427* (2013.01); *B65H 2553/30* (2013.01); *B65H 2557/61* (2013.01); *B65H 2557/63* (2013.01); *B65H 2801/06* (2013.01); *B65H 2801/39* (2013.01); *G01N 2291/011* (2013.01); *G01N 2291/015* (2013.01); *G01N 2291/0237* (2013.01); *G01N 2291/048* (2013.01); *G01N 2291/102* (2013.01)

(58) Field of Classification Search
CPC .... B65H 7/125; B65H 2553/30; G01N 29/11; G01N 29/4427; G01N 29/07
See application file for complete search history.

(56) References Cited

U.S. PATENT DOCUMENTS

| | | | |
|---|---|---|---|
| 8,387,865 B2 * | 3/2013 | Russell | .................... B65H 7/12 235/375 |
| 8,439,349 B2 | 5/2013 | Matsumoto et al. | |
| 8,500,114 B2 | 8/2013 | Matsumoto et al. | |

(Continued)

FOREIGN PATENT DOCUMENTS

JP         2012-188177 A    10/2012

*Primary Examiner* — Jeremy R Severson
(74) *Attorney, Agent, or Firm* — Fitzpatrick, Cella, Harper & Scinto

(57) ABSTRACT

A transmitter transmits ultrasound to the conveyance path. A receiver receives the ultrasound. A double-feed detector detects whether or not double-feed of a plurality of sheets has occurred. A controller causes the transmitter to transmit ultrasound at a first burst interval when determining the threshold value, and causes the transmitter to transmit ultrasound at a second burst interval, which is shorter than the first burst interval, when detecting the double-feed of sheets. A double-feed detector determines a threshold value that enables distinction between double-feed and single-feed.

12 Claims, 13 Drawing Sheets

(56) References Cited

U.S. PATENT DOCUMENTS

| | | | |
|---|---|---|---|
| 8,678,383 B2* | 3/2014 | Niwano | B65H 7/125 |
| | | | 271/262 |
| 8,684,346 B2 | 4/2014 | Yamazaki et al. | |
| 8,752,830 B2* | 6/2014 | Fukusaka | B65H 3/46 |
| | | | 271/258.01 |
| 8,882,373 B2* | 11/2014 | Inoue | B65H 7/125 |
| | | | 400/582 |
| 9,027,919 B2 | 5/2015 | Fukusaka et al. | |
| 2004/0081022 A1* | 4/2004 | Arai | B65H 23/0204 |
| | | | 367/124 |
| 2006/0000889 A1* | 1/2006 | Ma | B65H 7/125 |
| | | | 235/381 |
| 2006/0145412 A1* | 7/2006 | Tagawa | B65H 7/125 |
| | | | 271/258.01 |
| 2014/0327925 A1* | 11/2014 | Hongo | B65H 7/06 |
| | | | 358/1.14 |
| 2015/0260688 A1* | 9/2015 | Ono | G01N 29/11 |
| | | | 73/599 |
| 2016/0159597 A1* | 6/2016 | Hayashi | B65H 7/04 |
| | | | 271/265.04 |

* cited by examiner

F I G. 4A
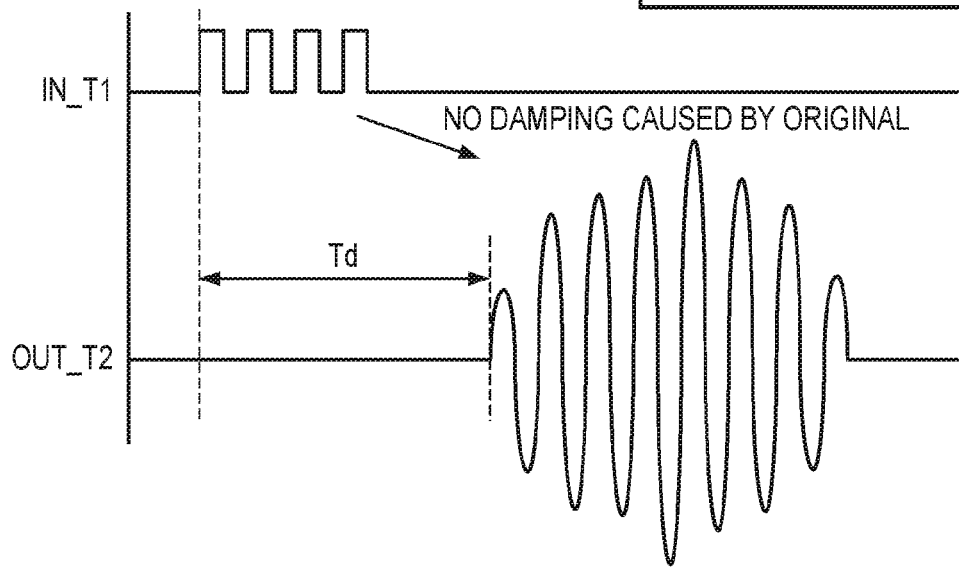
F I G. 4B
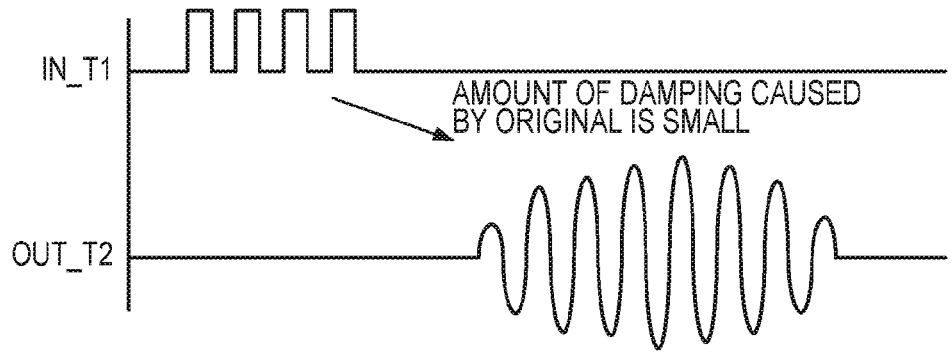
F I G. 4C
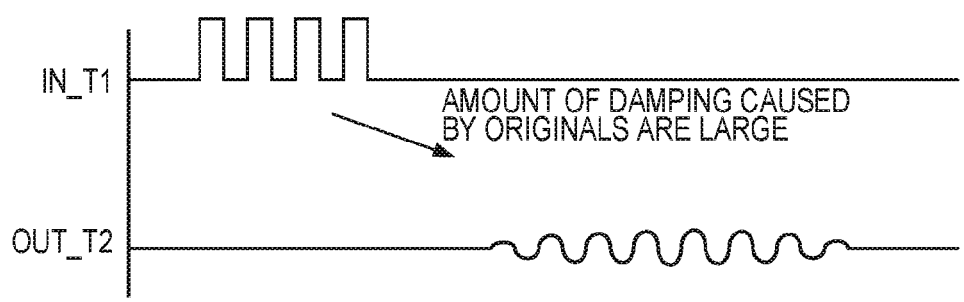

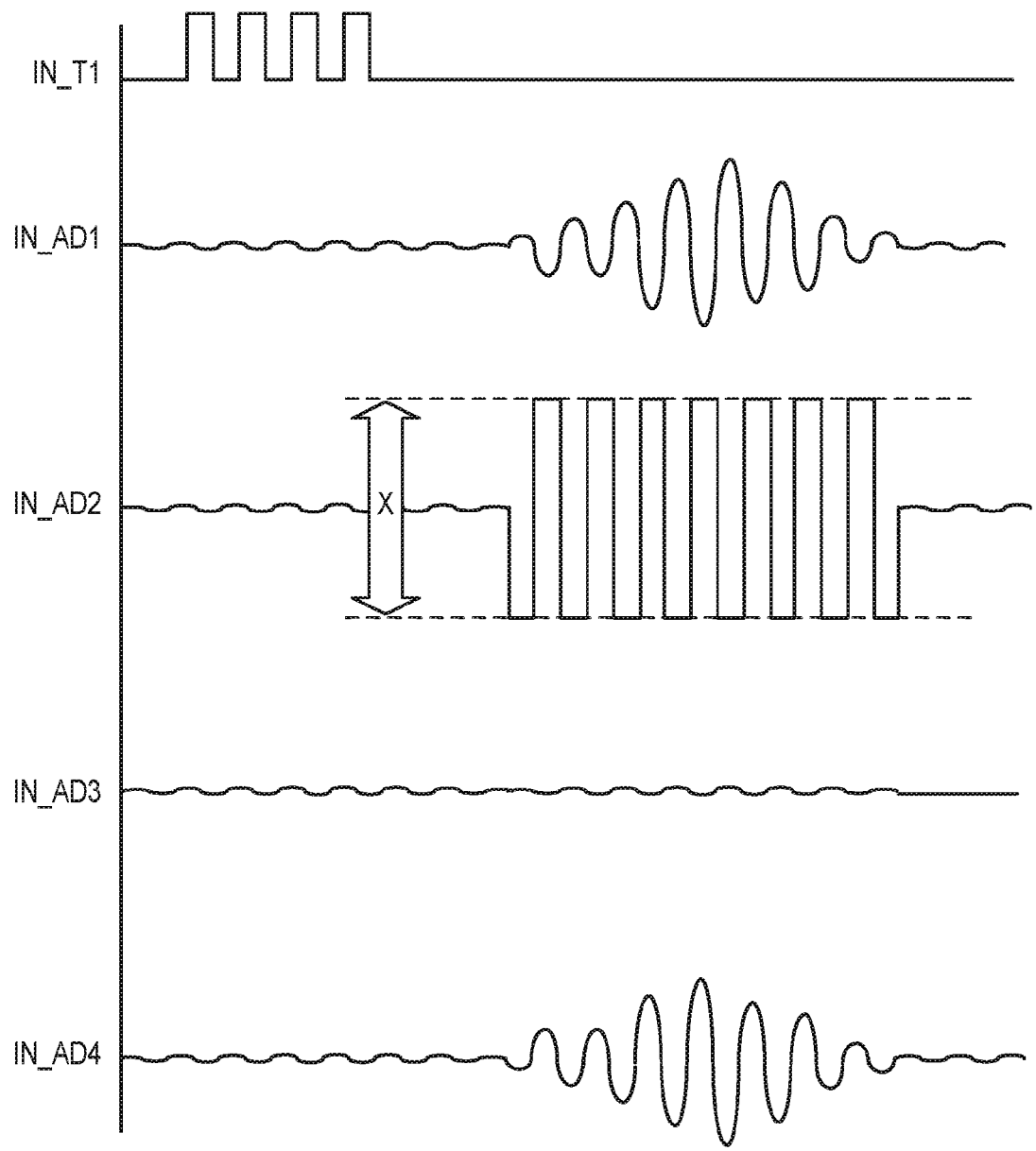

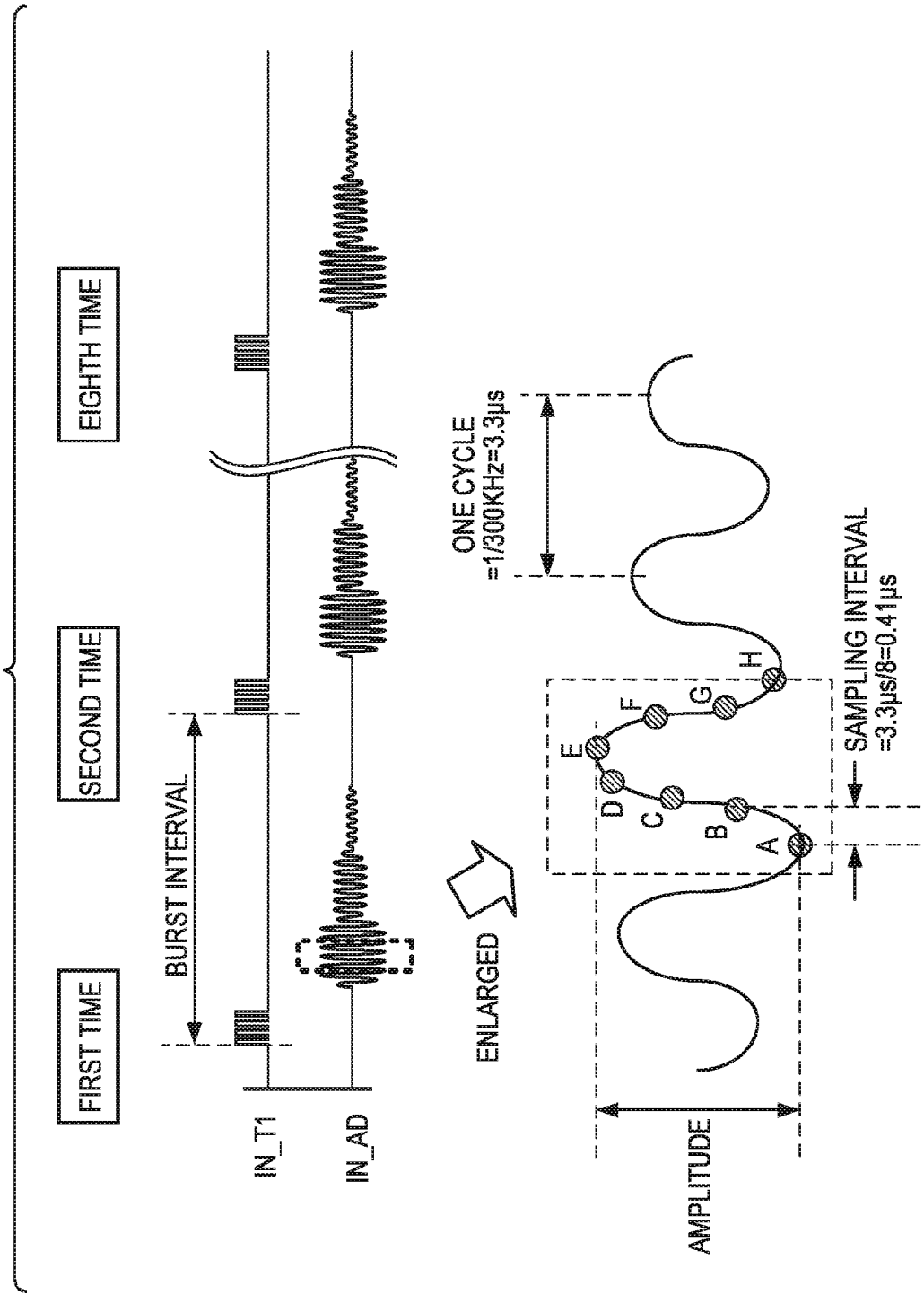

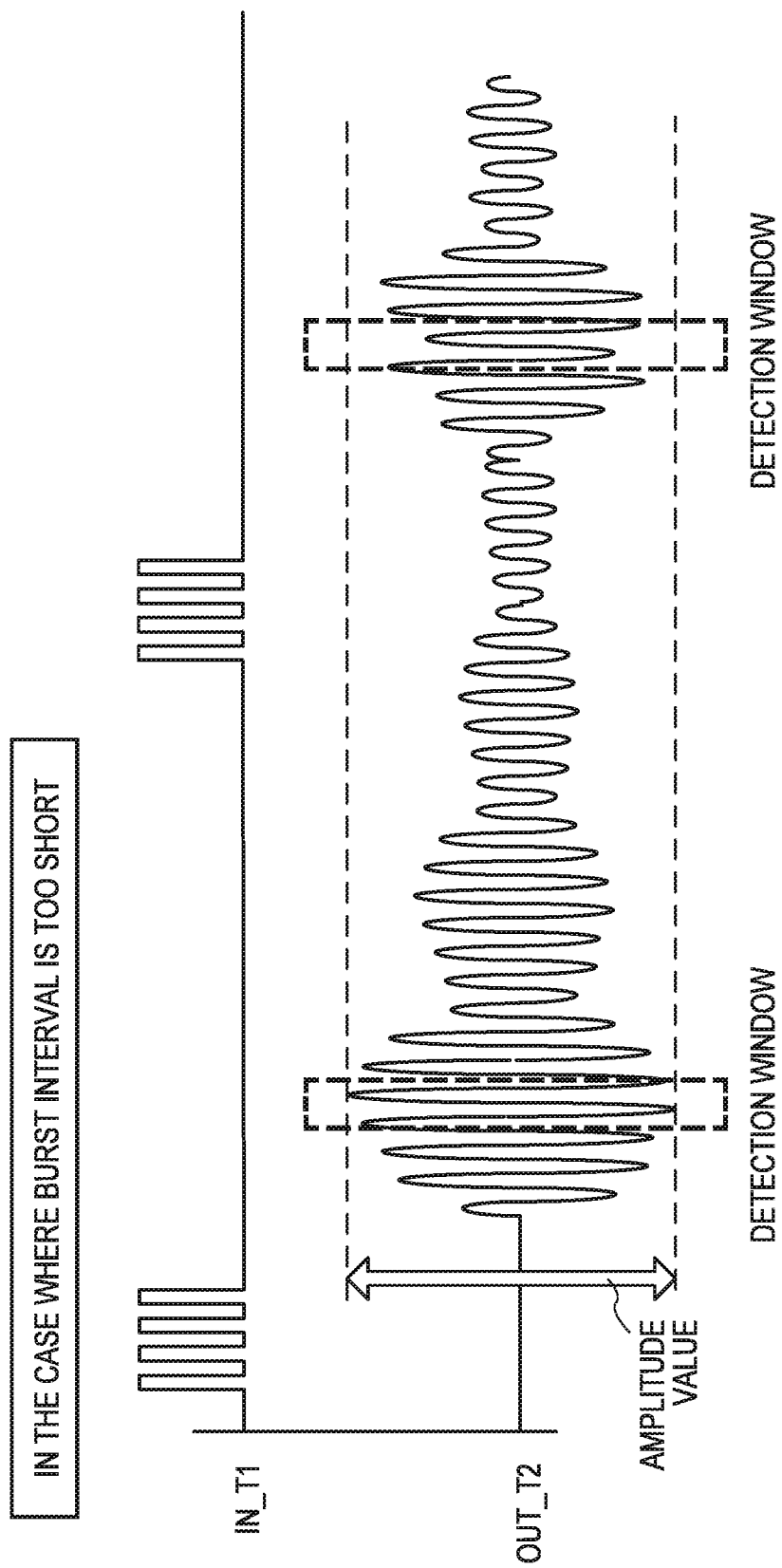

FIG. 10

| SAMPLING POINT | AD CONVERSION VALUE | | | | | | | | AVERAGE VALUE |
|---|---|---|---|---|---|---|---|---|---|
| | FIRST TIME | SECOND TIME | THIRD TIME | FOURTH TIME | FIFTH TIME | SIXTH TIME | SEVENTH TIME | EIGHTH TIME | |
| A | A[1] | A[2] | A[3] | A[4] | A[5] | A[6] | A[7] | A[8] | A[ave] |
| B | B[1] | B[2] | B[3] | B[4] | B[5] | B[6] | B[7] | B[8] | B[ave] |
| C | C[1] | C[2] | C[3] | C[4] | C[5] | C[6] | C[7] | C[8] | C[ave] |
| D | D[1] | D[2] | D[3] | D[4] | D[5] | D[6] | D[7] | D[8] | D[ave] |
| E | E[1] | E[2] | E[3] | E[4] | E[5] | E[6] | E[7] | E[8] | E[ave] |
| F | F[1] | F[2] | F[3] | F[4] | F[5] | F[6] | F[7] | F[8] | F[ave] |
| G | G[1] | G[2] | G[3] | G[4] | G[5] | G[6] | G[7] | G[8] | G[ave] |
| H | H[1] | H[2] | H[3] | H[4] | H[5] | H[6] | H[7] | H[8] | H[ave] |

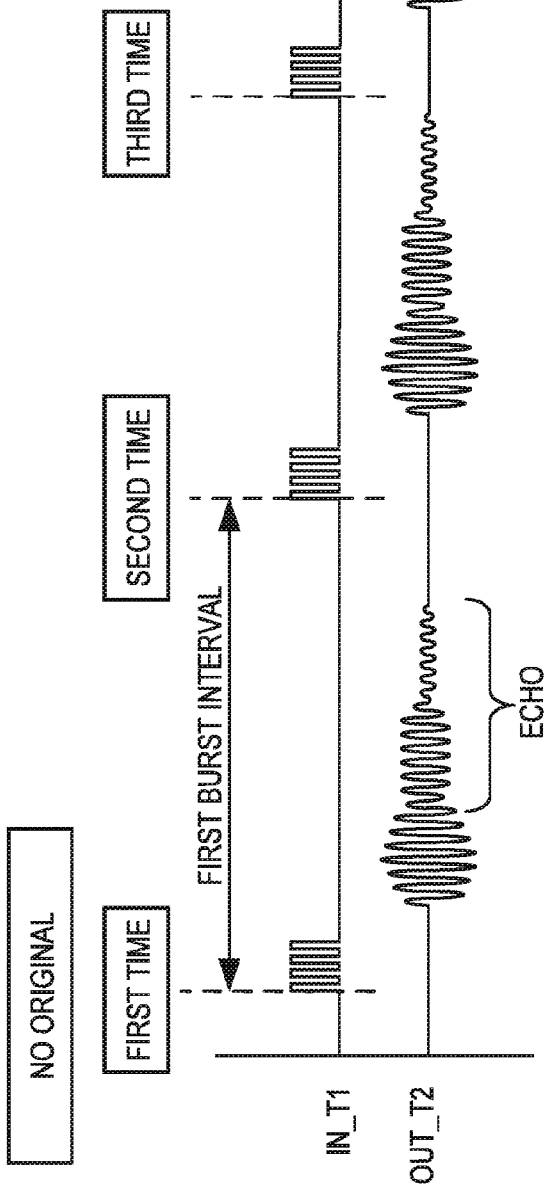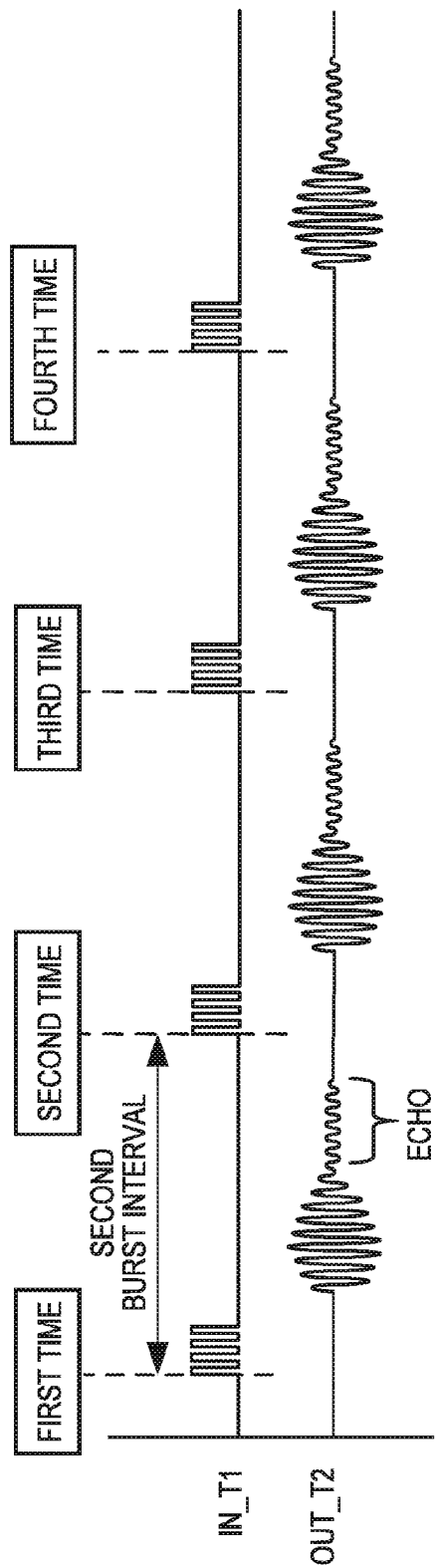

SHEET CONVEYANCE APPARATUS THAT DETECTS OVERLAPPING OF PLURALITY OF SHEETS, AND IMAGE READING APPARATUS

BACKGROUND OF THE INVENTION

Field of the Invention

The present invention relates to a technique for detecting overlapping of a plurality of sheets with a sheet conveyance apparatus or the like.

Description of the Related Art

A sheet conveyance apparatus for conveying sheets is used in image forming apparatuses and image reading apparatuses. It is presumed that sheets are conveyed one by one (which will be called "single-feed"), and conveyance of the sheets stops if a plurality of sheets are conveyed in an overlapping manner (which will be called "double-feed"). Japanese Patent Laid-Open No. 2012-188177 proposes an ultrasonic sensor for detecting double-feed. In particular, Japanese Patent Laid-Open No. 2012-188177 proposes changing the degree of amplification (gain) of a received signal in accordance with sensitivity variation in the ultrasonic sensor.

Incidentally, a signal that is output by an ultrasonic sensor is amplified by an amplifying circuit, but the detection accuracy may decrease due to noise components such as exogenous noise and semiconductor noise. In order to reduce the influence of noise, performing burst transmission of ultrasound (ultrasonic waves) multiple times and averaging the detection results is effective. However, if burst transmission is performed, an echo remains for a certain period of time, and accordingly, the next burst transmission cannot be performed until the echo has disappeared. Note that a time interval between the preceding burst transmission and the subsequent burst transmission will be called a burst interval. That is to say, the burst interval refers to the time from the timing at which the preceding burst transmission starts until the timing at which the subsequent burst transmission starts. If a long burst interval is set, the influence of an echo on the subsequent burst transmission is small. However, there may be cases where double-feed with a small amount of overlapping between the preceding sheet and the subsequent sheet (i.e., dragged double-feed) cannot be detected. This is because, the longer the burst interval is, the lower the number of times that double-feed detection can be executed while one sheet is conveyed is. A threshold value that is used for detecting double-feed is determined by performing burst transmission in a state where no sheet exists. When in a state where no sheet exists, an echo occurs over a long time, and therefore, the burst interval has to be long. On the other hand, in a state where a sheet exists, an echo occurs over a shorter time. Accordingly, if the burst interval used in a state where a sheet exists can be set shorter than the burst interval used in a state where no sheet exists, the number of times that burst transmission is performed for one sheet can be increased, and the accuracy of double-feed detection will improve. For example, dragged double-feed will also be able to be detected. The present invention enables more accurate detection of double-feed than with the conventional technique.

SUMMARY OF THE INVENTION

The present invention provides an sheet conveyance apparatus comprising the following elements. A conveyance unit conveys a sheet on a conveyance path; a transmitter configured to transmit ultrasound to the conveyance path. A receiver receives the ultrasound transmitted from the transmitter. The receiver is mounted opposing the transmitter. A double-feed detector detects whether or not double-feed of a plurality of sheets has occurred on the conveyance path by comparing, with a threshold value, an amplitude level of an output signal that is output from the receiver. A ultrasound controller causes the transmitter to transmit ultrasound at a first burst interval when determining the threshold value, and causes the transmitter to transmit ultrasound at a second burst interval, which is shorter than the first burst interval, when detecting the double-feed of sheets. The double-feed detector determines the threshold value that enables distinction between double-feed and single-feed, based on an amplitude level of an output signal that has been output by the receiver receiving the ultrasound transmitted at the first burst interval by the transmitter in a state where no sheet exists on the conveyance path.

Further features of the present invention will become apparent from the following description of exemplary embodiments (with reference to the attached drawings).

BRIEF DESCRIPTION OF THE DRAWINGS

FIGS. 4A to 4C are diagrams showing the principle of double-feed detection.

FIG. 6 is a diagram showing an example of amplitude values of output signals corresponding to the presence of an original.

FIG. 8 is a diagram illustrating sampling points.

FIG. 9 is a diagram illustrating influence of an echo.

FIG. 10 is a diagram illustrating a method for determining amplitude.

FIGS. 12A and 12B are diagrams illustrating a difference between burst intervals.

DESCRIPTION OF THE EMBODIMENTS

An embodiment of an image reading apparatus will be described with reference to the drawings. Note that an image reading apparatus may be a stand-alone image scanner, an image scanner connected to a network, a facsimile apparatus, a copying machine, or a multifunctional machine. A sheet conveyance apparatus may be mounted in an image forming apparatus.

Image Reading Apparatus

Figure 1:
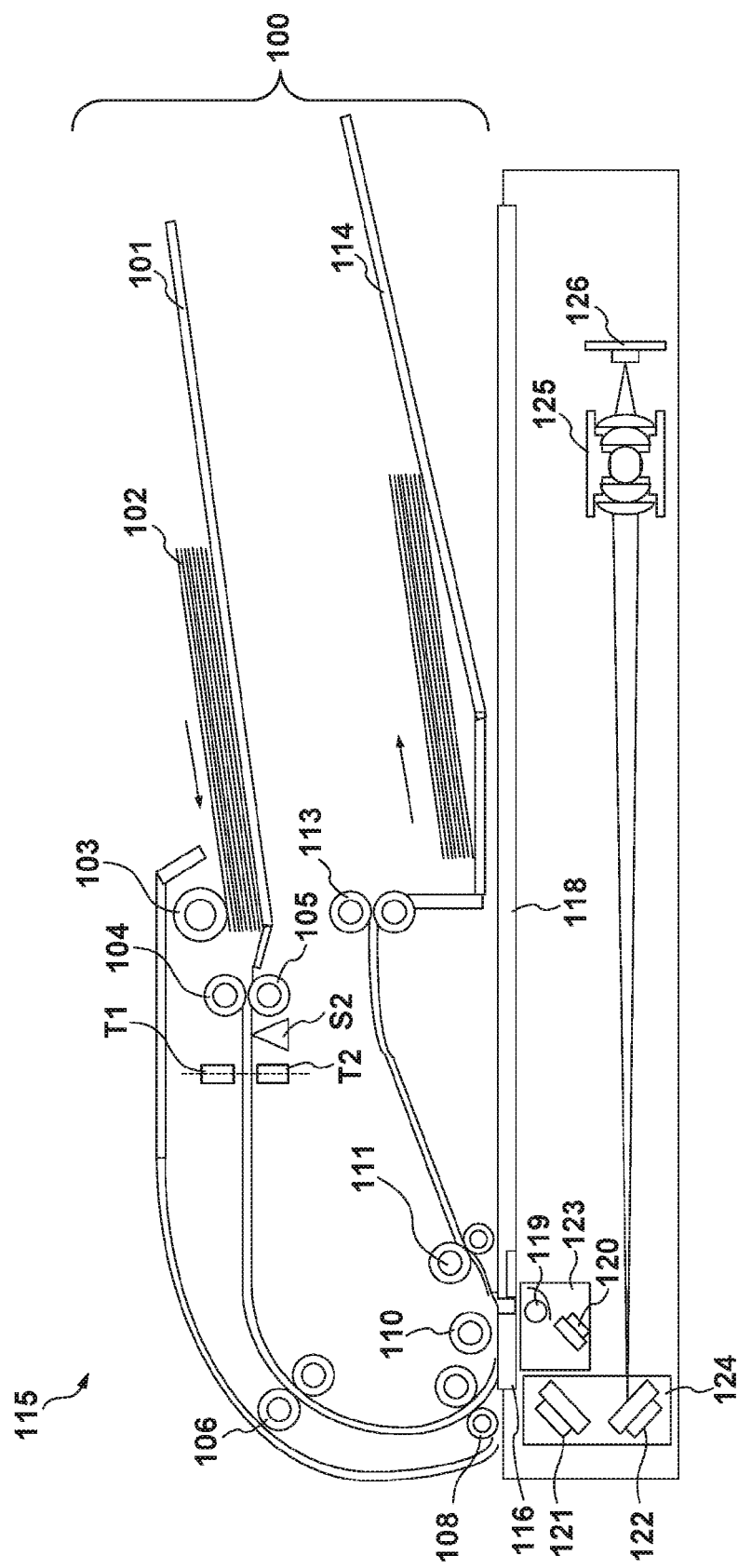
FIG. 1 is a diagram showing a configuration of a sheet conveyance apparatus.

In FIG. 1, an image reading apparatus 115 has a sheet conveyance apparatus 100. An original tray 101 is an original holder on which one or more sheets (originals 102) are placed. A feed roller 103 is provided downstream to the original tray 101 in a conveyance direction of the originals 102. The feed roller 103 is connected to the same driving source as that of a separation roller 104, and rotates with the rotation of the separation roller 104 to feed the originals 102. A follower roller 105 is arranged opposing the separation roller 104, and is pressed against the separation roller 104. The follower roller 105 may be made of a rubber material or the like that causes slightly less friction than that of the separation roller 104, for example. The follower roller 105 operates in conjunction with the separation roller 104 to convey the originals 102 that are fed by the feed roller 103 while the originals 102 are separated from one another.

A sheet sensor S2 is a sensor for detecting the time when each original 102 has passed through the follower roller 105 and the separation roller 104. An ultrasound transmitting portion (ultrasound transmitting element) T1 and an ultrasound receiving portion (ultrasound receiving element) T2 are arranged opposing each other with a conveyance path therebetween. Whether or not the originals 102 are overlapping each other is detected by the ultrasound receiving portion T2 receiving ultrasound transmitted by the ultrasound transmitting portion T1.

A registration roller pair 106 includes conveyance rollers that correct a skew of the originals 102. A read roller pair 108 includes conveyance rollers that convey the originals 102 to a moving-sheet reading glass 116. A platen guide 110 is arranged opposing the moving-sheet reading glass 116. Image information regarding a surface of each original 102 that passes over the moving-sheet reading glass 116 is read by an image sensor 126. A read discharge roller pair 111 includes conveyance rollers that convey each original 102 toward a discharge roller pair 113 after the image sensor 126 finishes reading the original 102. The discharge roller pair 113 includes conveyance rollers that discharge the originals 102 to a discharge tray 114. Note that these conveyance rollers function as a conveyance unit that conveys sheets on the conveyance path.

The main body of the image reading apparatus 115 has an original holder glass 118, a first mirror holder 123, a second mirror holder 124, a lens 125, the image sensor 126, and the like. The first mirror holder 123 has a light source 119 that emits light to a side of each original 102 to be read with light, and a mirror 120 for guiding reflected light from the original 102 to the image sensor 126. The second mirror holder 124 has mirrors 121 and 122 for guiding reflected light from each original 102 to the image sensor 126. The original 102 placed on the original holder glass 118 is read by the first mirror holder 123 and the second mirror holder 124 moving parallel with the original holder glass 118. The image sensor 126 performs, using a light-receiving device, photoelectric conversion on the reflected light that forms an image through the lens 125, and outputs an electric signal corresponding to the amount of incident light.

Controller

A controller that controls the image reading apparatus 115 will be described using FIG. 2. A CPU 201 controls the image reading apparatus 115 in accordance with a control program stored in a ROM in a memory 206. The memory 206 also has a RAM. The CPU 201 drives various conveyance rollers in the sheet conveyance apparatus 100 by controlling a motor 202. The CPU 201 also detects the arrival time of each original 102 using the sheet sensor S2 and controls operation timing of the ultrasound transmitting portion T1, the ultrasound receiving portion T2, an AD converter 205, and the like.

An ultrasonic transmission circuit (transmitter) 210 has a drive circuit 203 and an ultrasound transmitting portion T1. The drive circuit 203 receives, from the CPU 201, a burst signal having a frequency (300 KHz in this embodiment) that is close to a resonance frequency of the ultrasound transmitting portion T1 and the ultrasound receiving portion T2, and converts this burst signal into a burst signal having a voltage necessary for driving the ultrasound transmitting portion T1. The ultrasound transmitting portion T1 transmits ultrasound in accordance with the burst signal from the drive circuit 203.

An ultrasound receiving circuit (receiver) 220 has an ultrasound receiving portion T2, an amplifier 204, and the AD converter 205. The ultrasound receiving portion T2 receives the ultrasound transmitted from the ultrasound transmitting portion T1, generates an electric signal corresponding to the amplitude of the received ultrasound, and outputs the generated electric signal to the amplifier 204. The amplifier 204 amplifies the signal output from the ultrasound receiving portion T2 and outputs the amplified signal to the AD converter 205. The AD converter 205 performs AD conversion on the signal that has been amplified by the amplifier 204, in accordance with a timing signal that is output from the CPU 201, and outputs the result of this AD conversion to the CPU 201.

The CPU 201 calculates an amplitude level of the received ultrasound from the output of the AD converter 205, and detects double-feed of the originals 102 based on the amplitude level. For example, the CPU 201 functions as an ultrasound control portion (ultrasound controller) 211 and a double-feed detecting portion (double-feed detector) 212 by executing a control program. When determining a threshold value, the ultrasound control portion 211 causes the ultrasound transmitting portion T1 to transmit ultrasound at a first burst interval. When detecting double-feed of sheets, the ultrasound control portion 211 causes the ultrasound transmitting portion T1 to transmit ultrasound at a second burst interval, which is shorter than the first burst interval. The double-feed detecting portion 212 detects whether or not double-feed of a plurality of sheets has occurred on the conveyance path by comparing, with the threshold value, the amplitude level of the output signal that is output from the ultrasound receiving circuit 220. The double-feed detecting portion 212 further determines a threshold value that enables distinction between double-feed and single-feed, based on the amplitude level of the output signal that has been output by the receiving circuit 220 receiving the ultrasound transmitted at the first burst interval by the ultrasound transmitting portion T1 in a state where no sheet exists on the conveyance path. Note that some or all of these functions may be implemented by hardware such as an ASIC or an FPGA. ASIC is an abbreviation for application specified IC. FPGA is an abbreviation for field programmable gate array. Data necessary for control (such as the threshold value for double-feed determination and coefficients for calculating the threshold value) is stored in the memory 206.

Installation Angle of Ultrasonic Sensor

Figure 3:
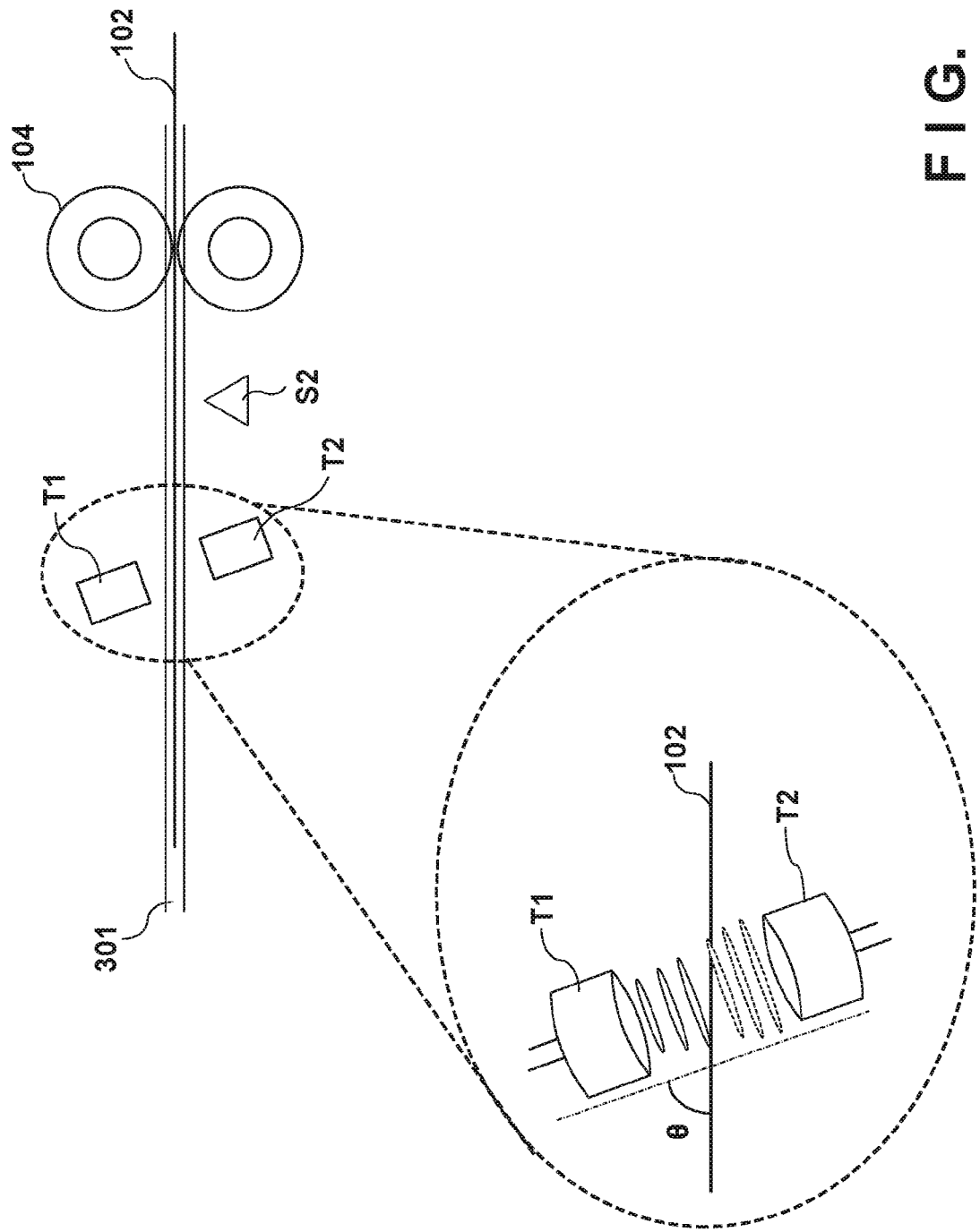
FIG. 3 is a diagram showing details of the vicinity of an ultrasonic sensor.

FIG. 3 is an enlarged view of the vicinity of the ultrasonic sensor including the ultrasound transmitting portion T1 and the ultrasound receiving portion T2. In this embodiment, the ultrasound transmitting portion T1 and the ultrasound receiving portion T2 are fixed (mounted) so as to tilt relative to a conveyance path 301 along which the originals 102 are conveyed. As shown in FIG. 3, the angle formed between the conveyance path 301 and a line (an exit axis of ultrasound) connecting the ultrasound transmitting portion T1 to the ultrasound receiving portion T2 is an installation angle θ. That is to say, the ultrasound transmitting portion T1 is an exemplary transmission unit that is fixed (mounted) obliquely relative to the conveyance path and transmits ultrasound. The ultrasound receiving portion T2 is an exemplary receiving unit (an output unit that outputs an output signal corresponding to the amplitude of ultrasound) that is fixed obliquely relative to the conveyance path and opposing the ultrasound transmitting portion T1, and receives the ultrasound transmitted from the ultrasound transmitting portion T1. With this tilted arrangement, the influence of an echo is smaller than with an arrangement in which the exit axis (incident axis) is perpendicular to the conveyance surface of the conveyance path 301, and accordingly, the accuracy of double-feed detection improves. Note that, in the case of perpendicular arrangement, an echo is likely to continue since ultrasound is repeatedly reflected between the ultrasound receiving portion T2 and the original 102. The installation angle θ is determined through experiments and simulations so as to maximize the detection accuracy. Thus, the installation angle θ is determined such that the conveyance surface of the conveyance path 301 is not perpendicular to the exit axis (incident axis) of ultrasound. In other words, the installation angle θ is determined such that the normal vector of the conveyance surface is not parallel with the exit axis (incident axis) of ultrasound. In the case where a conveyance guide that guides the originals 102 is provided on the conveyance path 301, the ultrasound transmitting portion T1 and the ultrasound receiving portion T2 are arranged at positions where the conveyance guide does not exist. Alternatively, the ultrasound transmitting portion T1 and the ultrasound receiving portion T2 may be installed so as to directly face each other via a cutout (hole) provided in the conveyance guide.

The ultrasound transmitted from the ultrasound transmitting portion T1 penetrates through the original 102 and propagates to the ultrasound receiving portion T2. The ultrasound receiving portion T2 converts the degree of intensity of the received ultrasound into voltage amplitude, and outputs this voltage amplitude to the amplifier 204. The amplifier 204 amplifies the output signal from the ultrasound receiving portion T2, and the CPU 201 receives a digital value obtained by AD conversion performed by the AD converter 205. The CPU 201 detects whether or not double-feed of the originals 102 has occurred by comparing the digital value indicating the amplitude level with the predetermined threshold value.

Method for Detecting Double-Feed

FIGS. 4A to 4C are diagrams illustrating a mechanism for distinguishing between single-feed and double-feed of the originals using the ultrasonic sensor. FIG. 4A shows a driving signal IN_T1 and an output signal OUT_T2 in a state where no original exists between the ultrasound transmitting portion T1 and the ultrasound receiving portion T2. The driving signal IN_T1 is a signal that is input to the ultrasound transmitting portion T1 from the drive circuit 203. The driving signal IN_T1 is a burst signal that includes a continuous rectangular wave. The output signal OUT_T2 is a signal that the ultrasound receiving portion T2 outputs to the amplifier 204. FIG. 4B shows the driving signal IN_T1 and the output signal OUT_T2 in a state where one original (single-feed) exists between the ultrasound transmitting portion T1 and the ultrasound receiving portion T2. FIG. 4C shows the driving signal IN_T1 and the output signal OUT_T2 in a state where two originals (double-feed) exist between the ultrasound transmitting portion T1 and the ultrasound receiving portion T2.

A delay time Td occurs from a burst signal start timing of the driving signal IN_T1 until a start timing of the output signal OUT_T2. The delay time Td is a propagation time required for propagation of ultrasound from the ultrasound transmitting portion T1 to the ultrasound receiving portion T2.

As can be understood from a comparison between FIG. 4A and FIG. 4B, if one original 102 exists between the ultrasound transmitting portion T1 and the ultrasound receiving portion T2, ultrasound is dampened, and therefore the amplitude of the output signal OUT_T2 decreases. As can be understood from a comparison between FIG. 4B and FIG. 4C, if two originals 102 exist between the ultrasound transmitting portion T1 and the ultrasound receiving portion T2, the ultrasound is dampened every time the ultrasound penetrates through an original, and therefore the amplitude of the output signal OUT_T2 further decreases. Accordingly, the CPU 201 can distinguish between single-feed and double-feed by comparing the amplitude of the output signal OUT_T2 with the predetermined threshold value.

Note that the damping amount of ultrasound also differs depending on the thickness and the type of the originals 102. However, compared with the change in damping amount occurring due to the thickness and the type of the originals 102, the difference in the damping amount occurring due to the difference in the number of originals 102 (one or a plurality of originals) is considerably large. Accordingly, the CPU 201 can detect double-feed regardless of the thickness and the type of the originals 102.

Amplifier and AD Converter

Figure 5:
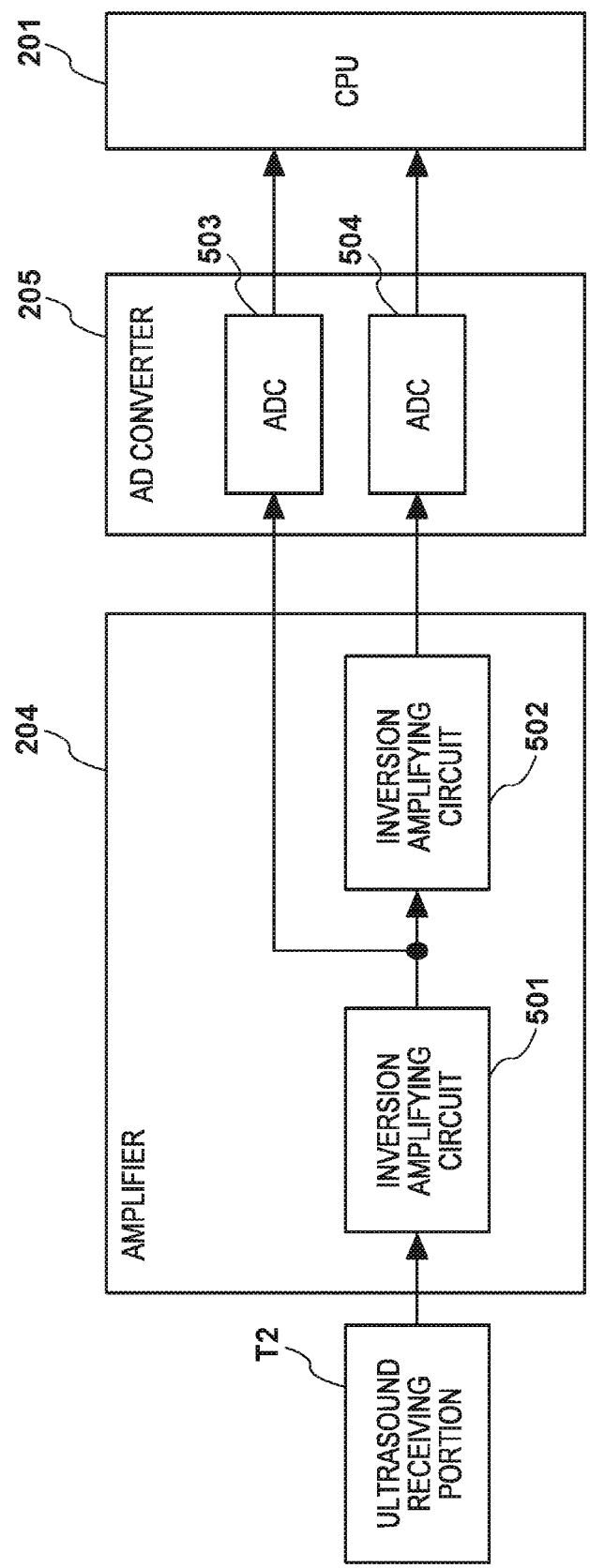
FIG. 5 is a diagram showing details of an amplifier and an AD converter.

FIG. 5 is a diagram showing details of the amplifier 204 and the AD converter 205. The amplifier 204 has multi-stage amplifying circuits in order to greatly amplify the small output signal OUT_T2 from the ultrasound receiving portion T2. According to FIG. 5, as an example, the amplifier 204 is constituted by two-stage amplifying circuits, namely inversion amplifying circuits 501 and 502. Note that the inside of the inversion amplifying circuits 501 and 502 each may be constituted by multi-stage amplifying circuits. The output of the inversion amplifying circuit 501 is input to an AD conversion circuit 503, and the output of the inversion amplifying circuit 502 is input to an AD conversion circuit 504. The damping amount and the propagation time of ultrasound change due to sensitivity variation in the ultrasonic sensor, the ambient temperature of the ultrasonic sensor, and an fixing error between the ultrasound transmitting portion T1 and the ultrasound receiving portion T2. Accordingly, the CPU 201 detects the amplitude level of ultrasound in a state where no original exists between the ultrasound transmitting portion T1 and the ultrasound receiving portion T2, and adjusts the threshold value in accordance with the amplitude level. Also, the CPU 201 may adjust ultrasound sampling timing in accordance with ultrasound receiving timing at this time. However, as mentioned above, the damping amount of ultrasound differs greatly between when no original exists and when an original(s) exists, as shown in FIGS. 4A to 4C. For this reason, if the output signal OUT_T2 is amplified with the same degree of amplification, the output signal obtained in a state where no original exists is saturated in some cases. That is to say, the amplitude of the output signal is too large and exceeds an output voltage range of the amplifier 204 or exceeds an input voltage range of the AD converter 205. In such cases, the threshold value cannot be correctly determined. Alternatively, the amplitude of the output signal OUT_T2 obtained in a state where an original(s) exists is too small and buried in dark noise. In this case, single-feed and double-feed of the originals cannot be distinguished from each other.

Detection of ultrasound in a state where no original exists performed for determining the threshold value may be executed immediately before detecting the original(s). This will be advantageous in setting the same ambient temperature and positional relationship of the ultrasonic sensor when detecting the original(s) and when determining the threshold value. Giving consideration to this, the configuration of the amplifier 204 and the AD converter 205 shown in FIG. 5 is advantageous.

FIG. 6 is a diagram showing exemplary output signals that are output to the AD converter 205 from the amplifier 204. An input signal IN_AD1 is a signal that is output from the inversion amplifying circuit 501 and input to the AD conversion circuit 503 in a state where no original exists between the ultrasound transmitting portion T1 and the ultrasound receiving portion T2. An input signal IN_AD2 is a signal that is output from the inversion amplifying circuit 502 and input to the AD conversion circuit 504 in a state where no original exists between the ultrasound transmitting portion T1 and the ultrasound receiving portion T2. The input signal IN_AD1 is amplified by one inversion amplifying circuit, and is therefore not saturated. On the other hand, the input signal IN_AD2 is amplified by two inversion amplifying circuits, and is therefore saturated. Accordingly, the input signal IN_AD1 is employed for determining the threshold value. That is to say, the CPU 201 determines the threshold value using the output of the AD conversion circuit 503.

An input signal IN_AD3 is a signal that is output from the inversion amplifying circuit 501 and input to the AD conversion circuit 503 in a state where one original exists between the ultrasound transmitting portion T1 and the ultrasound receiving portion T2. An input signal IN_AD4 is a signal that is output from the inversion amplifying circuit 502 and input to the AD conversion circuit 504 in a state where one original exists between the ultrasound transmitting portion T1 and the ultrasound receiving portion T2. The input signal IN_AD3 is amplified by one inversion amplifying circuit, and is therefore not amplified to a sufficient amplitude level. On the other hand, the input signal IN_AD4 is amplified by two inversion amplifying circuits, and is therefore amplified to a sufficient amplitude level. Accordingly, the input signal IN_AD4 is employed for detecting double-feed. That is to say, the CPU 201 detects double-feed using the output of the AD conversion circuit 504. Note that the polarity of signals is inverted by the inversion amplifying circuits 501 and 502. However, the amplitude of the signals is used in double-feed detection, and therefore, the polarity inversion is not an issue.

Characteristics of ultrasound and a method for detecting double-feed will be described using FIGS. 7A and 7B. As mentioned above, the damping amount of ultrasound changes depending on sensitivity variation (individual difference) in the ultrasonic sensor, the ambient temperature, a fixing error, and the like. Accordingly, the threshold value for double-feed detection needs to be corrected in accordance with the change in the damping amount. The CPU 201 determines a correction coefficient for correcting the threshold value, using the amplitude level of ultrasound (i.e., the output of the AD conversion circuit 503) in a state where no original exists between the ultrasound transmitting portion T1 and the ultrasound receiving portion T2.

Figure 7A:
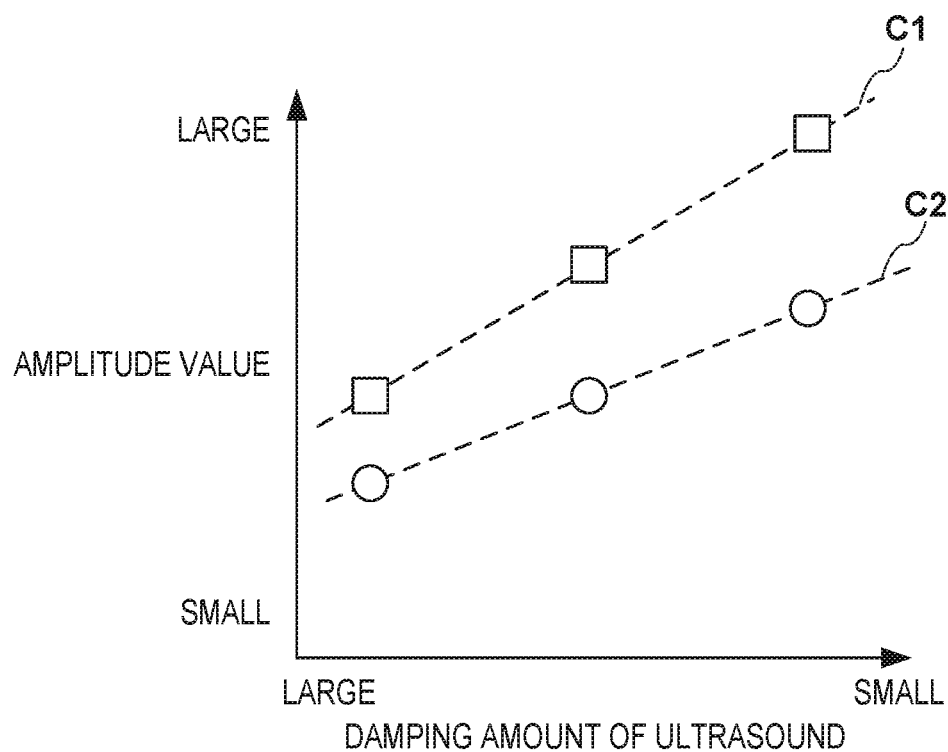
FIGS. 7A and 7B are diagrams respectively showing a relationship between a damping amount of ultrasound and an amplitude value, and a relationship between a damping amount of ultrasound and a ratio.

FIG. 7A shows a relationship between the damping amount of the ultrasound transmitted from the ultrasound transmitting portion T1 to the ultrasound receiving portion T2, and the amplitude value of the signal that is input to the AD converter 205. C1 denotes an amplitude characteristic of a signal that is input to the AD conversion circuit 503 in a state where no original exists between the ultrasound transmitting portion T1 and the ultrasound receiving portion T2. C2 denotes an amplitude characteristic of a signal that is input to the AD conversion circuit 504 in a state where one original exists between the ultrasound transmitting portion T1 and the ultrasound receiving portion T2. It can be understood that, in both cases, the larger the damping amount of ultrasound is, the smaller the amplitude value is, and the smaller the damping amount of ultrasound is, the larger the amplitude value is.

Figure 7B:
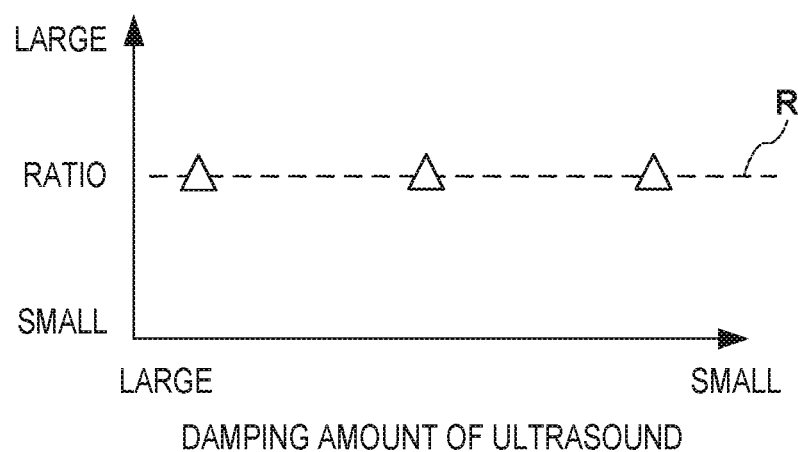

FIG. 7B is a diagram showing a ratio R between C1 and C2. As shown in FIG. 7B, even if the damping amount of ultrasound changes, the ratio between the amplitude value in a state where no original exists and the amplitude value in a state where an original exists is roughly fixed. That is to say, the CPU 201 can calculate, with high accuracy, the amplitude value in a state where an original exists by determining the amplitude value in a state where no original exists. Accordingly, the CPU 201 can accurately determine the threshold value for distinguishing between single-feed and double-feed by obtaining the amplitude value in a state where no original exists. The threshold value is determined or corrected so as to be a value between the amplitude value in the case of single-feed and the amplitude value in the case of double-feed.

FIG. 8 is a diagram illustrating details of amplitude calculation. The signal IN_AD, after being amplified by the amplifier 204, is input to the AD converter 205 and sampled. The CPU 201 outputs an operation start signal to the AD converter 205 at the time when a predetermined time has elapsed after the time when the driving circuit 203 was instructed to start to output the driving signal. The AD converter 205, upon receiving the operation start signal, samples the signal IN_AD at a predetermined sampling interval, converts the signal IN_AD into a digital value, and outputs the digital value to the CPU 201. As shown in FIG. 8, the sampling is executed for one cycle of the ultrasound (driving signal). For example, in the case of a driving signal of 300 KHz, 3.3 μs is one cycle. As shown in FIG. 8, the start timing of AD conversion is the time when the amplitude of the signal IN_AD is largest. Note that the time period in which the sampling is executed may also be called a detection window or an amplitude detection period.

In order to correctly detect the amplitude, the sampling interval needs to be sufficiently small relative to an ultrasound driving cycle (i.e., driving signal cycle). In this embodiment, ultrasound is generated by the driving signal having a frequency of 300 KHz, and accordingly, the cycle thereof is 3.3 μs. In the case of performing the sampling eight times in this cycle, the sampling interval is set to 0.41 μs. Thus, the sampling is performed at a sufficiently small sampling interval relative to the ultrasound driving cycle, the smallest value and the largest value are determined among the sampled values, a difference therebetween is obtained, and the amplitude of the received ultrasound for one arbitrary wave is thus obtained.

$$\text{Amplitude} = \text{MAX}(A,B,C,D,E,F,G,H) - \text{MIN}(A,B,C,D,E,F,G,H) \tag{1}$$

In FIG. 8, eight sample values A to H are obtained. MAX( ) denotes a function for determining the largest value, and MIN( ) denotes a function for determining the smallest value. In FIG. 8, the voltage value of the signal IN_AD is smallest at a sampling point A, and the voltage value is largest at a sampling point E. Accordingly, the amplitude is determined by subtracting the voltage value at the sampling point A from the voltage value at the sampling point E.

As mentioned above, the level of the output signal of the ultrasound receiving portion T2 is very small, and therefore, the degree of amplification of the amplifier 204 is set to a large degree of amplification. For this reason, the amplification is greatly affected by exogenous noise. Accurate amplitude cannot be obtained with only a sampling result for one cycle in some cases. For this reason, the CPU 201 obtains N sampling results at each sampling point by performing burst transmission of ultrasound N times, and executes statistical processing (e.g., average value calculation) for each sampling point. For example, N may be set to 8. The CPU 201 determines the largest value and the smallest value among the average values at each sampling point, and determines the difference therebetween to be the amplitude.

The shorter the burst interval is, the shorter the time taken for the sampling is, and the shorter the detection time required for one time of double-feed detection is. However, a problem occurs if the burst interval is excessively shortened. As shown in FIG. 9, the subsequent ultrasound is output in a state where an echo occurring due to the output of the preceding ultrasound remains, and therefore, the echo overlaps the subsequent ultrasound. This degrades the accuracy of the ultrasound detection result (amplitude). Accordingly, the burst interval needs to be set to a time with which the echo of the immediately preceding burst-driven ultrasound sufficiently decreases. Note that the burst interval may be set through experiments and simulations at the time of shipping of the image reading apparatus from a factory.

FIG. 10 shows an example where a received ultrasound wave is sampled at K (e.g. 8) sampling points within one detection window. Note that the voltage value is sampled N (e.g. 8) times at each sampling point. That is to say, burst transmission is executed N times.

The CPU 201 executes the sampling at the same sampling point for N times of burst transmission, and averages the results thereof. That is to say, for each of N times of burst transmission, the CPU 201 starts the sampling after a predetermined time period from the time of instructing the drive circuit 203 to output the driving signal. Thus, the phase (position) of the sampling point is the same for N times of the sampling. According to FIG. 10, the sample values of A[1] to A[8] are obtained at the sampling point A, and are averaged to obtain A[ave].

$$A[\text{ave}]=(A[1]+A[2]+A[3]+A[4]+A[5]+A[6]+A[7]+A[8])/8 \quad (2)$$

Even though ultrasound is transmitted and detected multiple times, almost no variation occurs in the sampling point in the time direction. For this reason, exogenous noise (i.e., variation in the amplitude direction) is reduced by the averaging.

Flowchart

Figure 11:
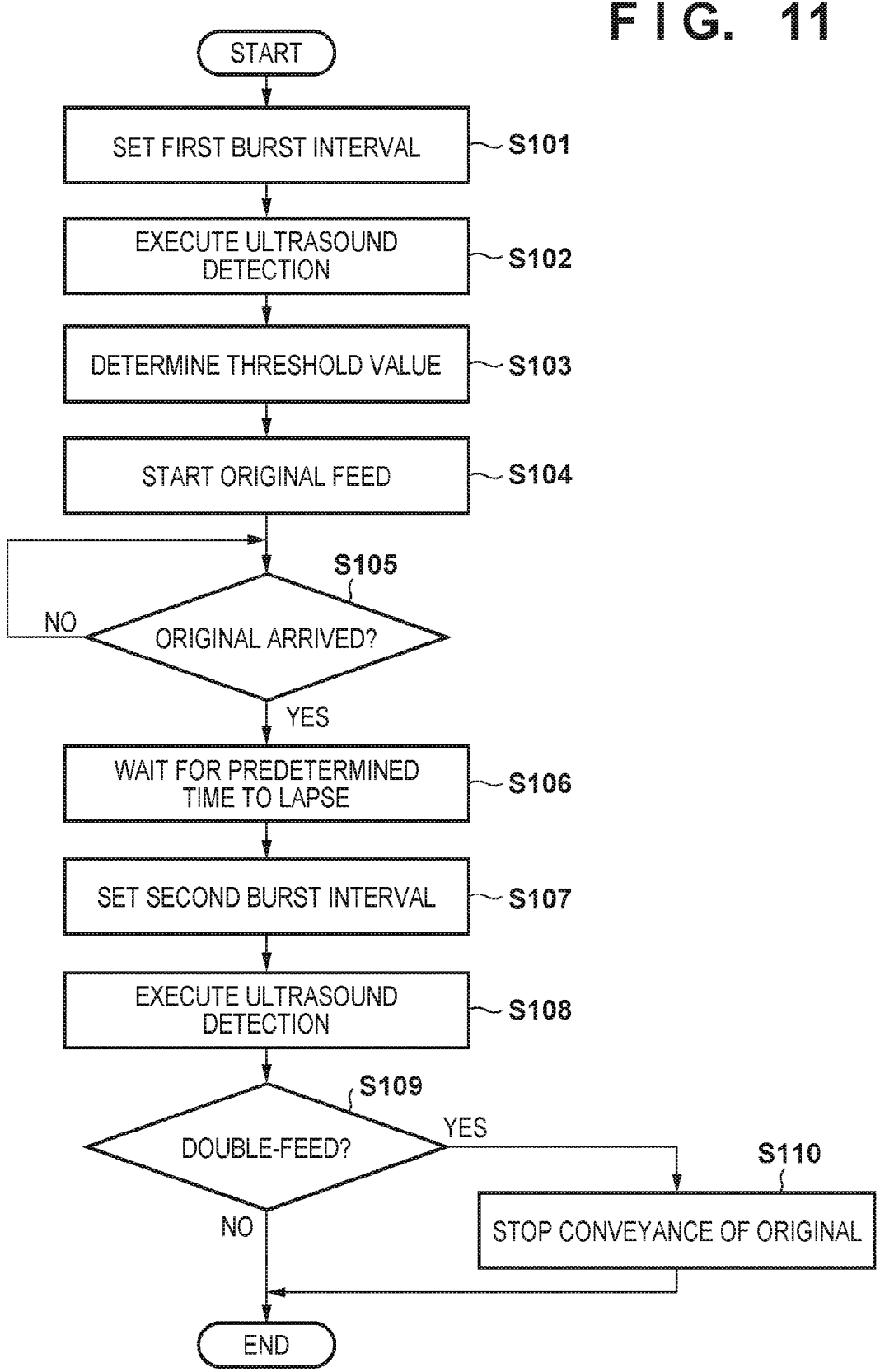
FIG. 11 is a flowchart of double-feed detection.

FIG. 11 is a flowchart of double-feed detection. This flow is entirely executed by the CPU 201 unless otherwise stated. The CPU 201, upon receiving an instruction to start to read an original 102 from an operating portion or the like, executes the following processing.

In step S101, the CPU 201 reads out the first burst interval, which serves as the ultrasound burst interval, from the memory 206 in order to determine the threshold value for double-feed detection, sets the read first burst interval, and outputs the burst signal at every first burst interval. The first burst interval is determined such that an echo becomes smaller than or equal to a tolerance limit, giving consideration to sensitivity variation in the ultrasonic sensor, a relative fixing position relationship between the ultrasound transmitting portion T1 and the ultrasound receiving portion T2, temperature, pressure, and the like. As mentioned above, the first burst interval is determined through experiments and simulations at the time of shipping from a factory. The drive circuit 203 converts the burst signal that has been input from the CPU 201 to generate the driving signal IN_T1, and outputs the driving signal IN_T1 to the ultrasound transmitting portion T1. The ultrasound transmitting portion T1 is driven by the driving signal IN_T1, and starts to transmit ultrasound.

In step S102, the CPU 201 starts to detect ultrasound. The CPU 201 sets the detection window at the time when a predetermined time has elapsed from the time when the output of the burst signal was started, and causes the AD conversion circuit 503 to execute the sampling at M sampling points. As mentioned above, this processing is repeated N times, and the CPU 201 obtains the average value of N sample values obtained at each sampling point, determines the largest value and the smallest value, and determines the amplitude from the difference between the largest value and the smallest value. The CPU 201 stores the amplitude in the RAM in the memory 206. Note that the signal to be sampled by the AD conversion circuit 503 is a signal that has been amplified by the inversion amplifying circuit 501. Saturation of the signal to be input to the AD conversion circuit 503 can thereby be suppressed.

In step S103, the CPU 201 determines the threshold value for double-feed detection based on the determined amplitude. As described using FIG. 7B, even if the damping amount of ultrasound changes, a ratio R between the amplitude in a state where an original exists and the amplitude in a state where no original exists is fixed. Accordingly, the CPU 201 determines the threshold value by multiplying the amplitude value stored in the memory 206 by a predetermined correction coefficient and stores the determined threshold value in the memory 206. The correction coefficient is 0.7, for example. To determine the correction coefficient, the original with which the damping amount of ultrasound is largest (i.e., the original with which the amplitude value of the output signal is smallest) is determined from among various originals that are available in the market, through experiments. Regarding this original, the amplitude in a state where an original exists and the amplitude where no original exists are measured, and the ratio R is obtained. The ratio R is multiplied by a margin Mg, and a correction coefficient E is determined. The possibility that double-feed is erroneously detected when thick sheet is conveyed is reduced using the margin Mg. An appropriate margin Mg is also determined through experiments and simulations.

In step S104, the CPU 201 drives the motor 202 for rotating various conveyance rollers and starts to feed and convey the original 102. In step S105, the CPU 201 determines whether or not a leading end of the original 102 has reached the sheet sensor S2, based on the detection signal of the sheet sensor S2. If the leading end of the original 102 has reached the sheet sensor S2, the CPU 201 proceeds to step S106. In step S106, the CPU 201 waits for a predetermined time Tw to lapse using a counter or a timer. This is for waiting for the original 102 to move from the detection position of the sheet sensor S2 to the detection position of the ultrasonic sensor. Therefore, the CPU 201 waits for the predetermined time Tw to lapse and thereafter proceeds to step S107.

In step S107, the CPU 201 reads out, from the memory 206, the second burst interval, which serves as the ultrasound burst interval for double-feed detection, sets the read second burst interval, and outputs the burst signal at every second burst interval. The second burst interval is shorter than the first burst interval. As mentioned above, the second burst interval is also determined through experiments and simulations at the time of shipping from a factory. The first burst interval is determined by executing experiments in a state where no original exists, whereas the second burst interval is determined by executing experiments in a state where an original exists. The second burst interval is also determined such that an echo becomes smaller than or equal to a tolerance limit, giving consideration to sensitivity variation in the ultrasonic sensor, a relative fixing position relationship between the ultrasound transmitting portion T1 and the ultrasound receiving portion T2, temperature, pressure, and the like. The drive circuit 203 converts the burst signal that is input from the CPU 201 to generate the driving signal IN_T1, and outputs the driving signal IN_T1 to the ultrasound transmitting portion T1. The ultrasound transmitting portion T1 is driven by the driving signal IN_T1, and starts to transmit ultrasound.

In step S108, the CPU 201 starts to detect ultrasound. The CPU 201 sets the detection window at the time when a predetermined time has elapsed from the time when the output of the burst signal was started, and causes the AD conversion circuit 504 to execute the sampling at M sampling points. The AD conversion circuit 504 is caused to execute the sampling because, if the original(s) 102 exists, the amplitude of the output signal OUT_T1 is small, and therefore a large degree of amplification is required. As mentioned above, this processing is repeated N times, and the CPU 201 obtains the average value of N sample values obtained at each of the M sampling points, determines the largest value and the smallest value of the M average values, and determines the amplitude from the difference between the largest value and the smallest value.

In step S109, the CPU 201 determines whether or not double-feed has occurred based on whether or not the amplitude value exceeds the threshold value. The CPU 201 determines that single-feed has occurred if the amplitude value exceeds the threshold value, and determines that double-feed has occurred if the amplitude value does not exceed the threshold value. If single-feed is detected, the CPU 201 skips step S110 and ends double-feed detection. That is to say, an image of this sheet is read. On the other hand, if double-feed is detected, the CPU 201 proceeds to step S110. In step S110, the CPU 201 stops the motor 202 to stop conveyance of the originals 102.

By shortening the burst interval used in a state where an original exists compared with the burst interval used in a state where no original exists, the double-feed detection time can be shortened. Even if dragged double-feed with a small amount of overlapping of originals occurs, the CPU 201 can detect this dragged double-feed.

FIG. 12A is a diagram showing a relationship between the driving signal IN_T1 and the output signal OUT_T2 from the ultrasound receiving portion T2 in a state where no original exists. FIG. 12B is a diagram showing a relationship between the driving signal IN_T1 and the output signal OUT_T2 from the ultrasound receiving portion T2 in a state where an original(s) exists. Comparing FIG. 12A with FIG. 12B, the second burst interval used in a state where an original(s) exists is shorter than the first burst interval used in a state where no original exists. Accordingly, ultrasound detection can be completed in a shorter time in a state where an original(s) exists than in a state where no original exists.

The double-feed detection time can be shortened compared with the conventional technique by employing the second burst interval. As a result of being able to shorten the double-feed detection time, double-feed with a small amount of overlapping, such as dragged double-feed in the case of which a trailing end of the preceding original overlaps a leading end of the subsequent original, can also be detected. Conventionally, there are cases where double-feed detection cannot be completed while an overlapping portion between the trailing end of the preceding original and the leading end of the subsequent original is passing through the ultrasonic sensor, and dragged double-feed cannot be accurately detected. In contrast, in this embodiment, dragged double-feed can also be accurately detected.

Reason Why Burst Interval Can Be Shortened

A description will be given, using FIGS. 12A, 12B, 13A, and 13B, of a reason why the second burst interval used in a state where an original(s) exists can be shortened compared with the first burst interval used in a state where no original exists. According to FIGS. 12A and 12B, it can be understood that the duration of an echo occurring in a state where an original(s) exists is shorter than the duration of an echo occurring in a state where no original exists. An echo is caused by multiple reflections of ultrasound that occur between the ultrasound transmitting portion T1 and the ultrasound receiving portion T2. In particular, the ultrasound receiving portion T2 that has received ultrasound reflects the ultrasound, and therefore functions as a secondary wave source.

Figure 13A:
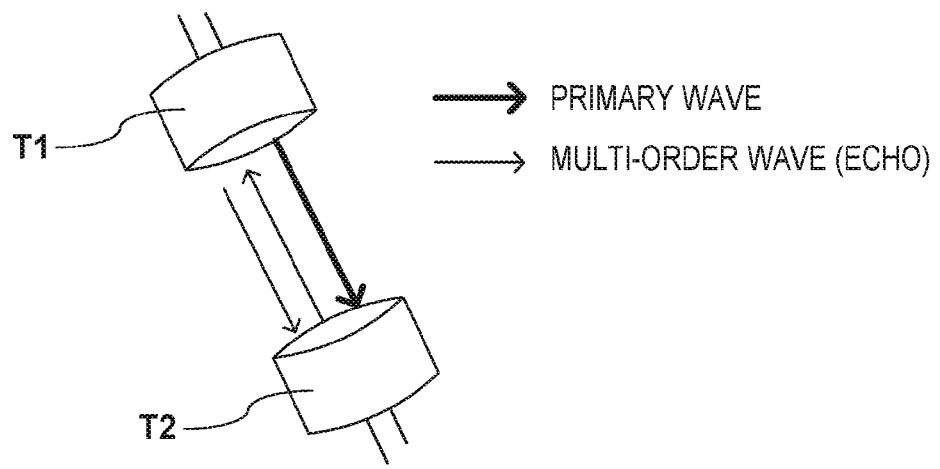
FIGS. 13A and 13B are diagrams illustrating the principle of occurrence of an echo.
Figure 13B:
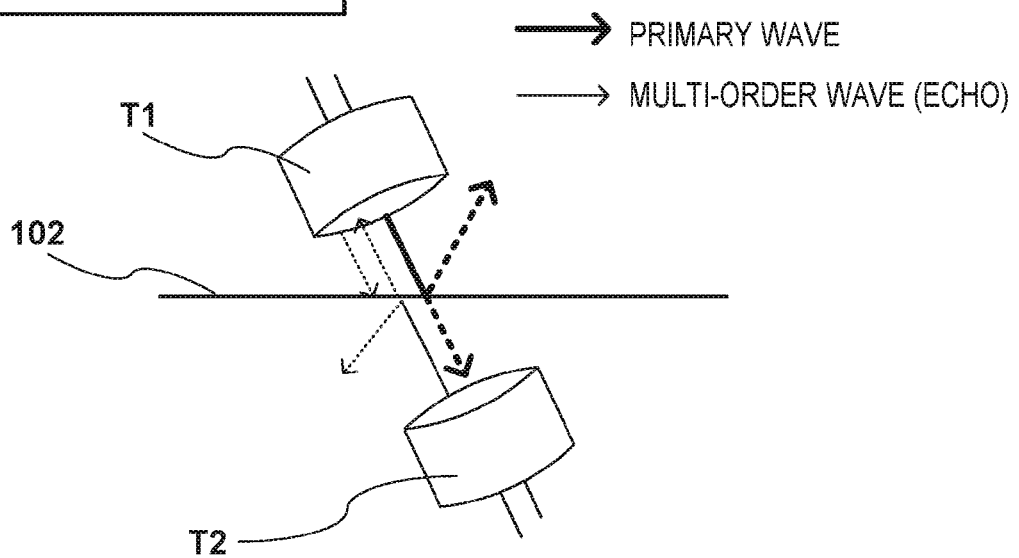

FIG. 13A shows how ultrasound propagates in a state where no original exists. FIG. 13B shows how ultrasound propagates in a state where an original exists. In both cases, the ultrasound transmitting portion T1 and the ultrasound receiving portion T2 are fixed obliquely relative to the conveyance path 301 along which the original 102 is conveyed.

As shown in FIG. 13A, in a state where no original exists, ultrasound (primary wave) transmitted by the ultrasound transmitting portion T1 first reaches the ultrasound receiving portion T2. Upon the ultrasound reaching the ultrasound receiving portion T2, a diaphragm provided in the ultrasound receiving portion T2 vibrates, this vibration is converted into electric energy, and the output signal OUT_T2 is generated. Simultaneously, the vibrated diaphragm serves as a secondary wave source, and ultrasound is output (reflected) in a direction extending toward the ultrasound transmitting portion T1. This ultrasound is reflected at the ultrasound transmitting portion T1 and returns to the ultrasound receiving portion T2. This action is repeated, and an echo continues until the ultrasound has sufficiently damped due to energy loss at the time of the reflection and the damping in the air.

On the other hand, in a state where an original exists as shown in FIG. 13B, a part of the ultrasound (primary wave) transmitted by the ultrasound transmitting portion T1 is reflected off the original 102, and the remaining part penetrates therethrough and reaches the ultrasound receiving portion T2. Upon the ultrasound reaching the ultrasound receiving portion T2, the diaphragm of the ultrasound receiving portion T2 vibrates, and the output signal OUT_T2 is generated. Simultaneously, the diaphragm serves as a secondary wave source, and ultrasound is output (reflected). The reflected ultrasound reaches the original 102, a part of this ultrasound is reflected, and the remaining part penetrates therethrough. The ultrasound that is reflected here propagates in another direction that is different from the direction extending toward the ultrasound transmitting portion T1 and the direction extending toward the ultrasound receiving portion T2. This is because the ultrasound transmitting portion T1 and the ultrasound receiving portion T2 are fixed obliquely relative to the conveyance path 301. Thus, only a part of the ultrasound that proceeds in the direction extending toward the ultrasound transmitting portion T1 that may cause an echo penetrates through the original 102, and accordingly, the intensity of the ultrasound that reaches the ultrasound transmitting portion T1 decreases significantly. That is to say, an echo decreases sufficiently in a shorter time in a state where an original exists than in a state where no original exists. As a result, the second burst interval used in a state where an original exists can be set shorter than the first burst interval used in a state where no original exists.

Summary

According to this embodiment, the CPU 201 functions as the ultrasound control portion 211 and the double-feed detecting portion 212 by executing a control program. When determining the threshold value, the ultrasound control portion 211 causes the ultrasound transmitting portion T1 to transmit ultrasound at the first burst interval. When detecting double-feed of sheets, the ultrasound control portion 211 causes the ultrasound transmitting portion T1 to transmit ultrasound at the second burst interval, which is shorter than the first burst interval. The double-feed detecting portion 212 detects whether or not double-feed of a plurality of sheets has occurred on the conveyance path by comparing, with the threshold value, the amplitude level of the output signal that is output from the ultrasound receiving circuit 220. The double-feed detecting portion 212 further determines the threshold value that enables distinction between double-feed and single-feed, based on the amplitude level of the output signal that has been output by the receiving circuit 220 receiving the ultrasound transmitted at the first burst interval by the ultrasound transmitting portion T1 in a state where no sheet exists on the conveyance path. In particular, the ultrasound control portion 211 causes the ultrasound transmitting portion T1 to transmit ultrasound at the first burst interval when determining the threshold value, and the ultrasound control portion 211 causes the ultrasound transmitting portion T1 to transmit ultrasound at the second burst interval, which is shorter than the first burst interval, when detecting double-feed of sheets. This configuration enables the number of times of double-feed detection executed per sheet to be increased compared with the conventional technique, and enables double-feed to be more accurately detected than with the conventional technique. For example, double-feed can be detected even if the area of the overlapping portion of sheets is small as in the case of dragged double-feed, which is a phenomenon in which a trailing end of the preceding sheet overlaps a leading end of the subsequent sheet.

The ultrasound control portion 211 may execute threshold value determination and double-feed detection within one conveyance job. That is to say, the ultrasound control portion 211 causes the ultrasound transmitting portion T1 to transmit ultrasound from the time when an instruction to convey a sheet is given until the sheet reaches a space between the ultrasound transmitting portion T1 and the ultrasound receiving portion T2 (i.e., in a state where the sheet does not exist on the conveyance path), and causes the double-feed detecting portion 212 to determine the threshold value. Upon the sheet reaching the space between the ultrasound transmitting portion T1 and the ultrasound receiving portion T2, the double-feed detecting portion 212 determines whether or not double-feed of a plurality of sheets has occurred, using the threshold value determined. This configuration can bring the state of the ultrasonic sensor at the time of threshold value determination to the state of the ultrasonic sensor at the time of double-feed detection, and improve the accuracy of double-feed detection.

As described using FIG. 12A, the first burst interval is the time required for an echo of the ultrasound transmitted from the ultrasound transmitting portion T1 to become smaller than or equal to a predetermined tolerance limit. This configuration enables accurate threshold value determination. As described using FIG. 12B, the second burst interval is the time required for an echo of the ultrasound transmitted from the ultrasound transmitting portion T1 to become smaller than or equal to a predetermined tolerance limit. This configuration enables accurate double-feed detection.

As described regarding step S103, the double-feed detecting portion 212 may determine the threshold value by multiplying the amplitude level obtained in a state where no sheet exists on the conveyance path by the correction coefficient. Also, the double-feed detecting portion 212 may determine the threshold value by multiplying the amplitude level obtained in a state where no sheet exists on the conveyance path by the correction coefficient and the margin. This configuration enables accurate threshold value determination.

Figure 2:
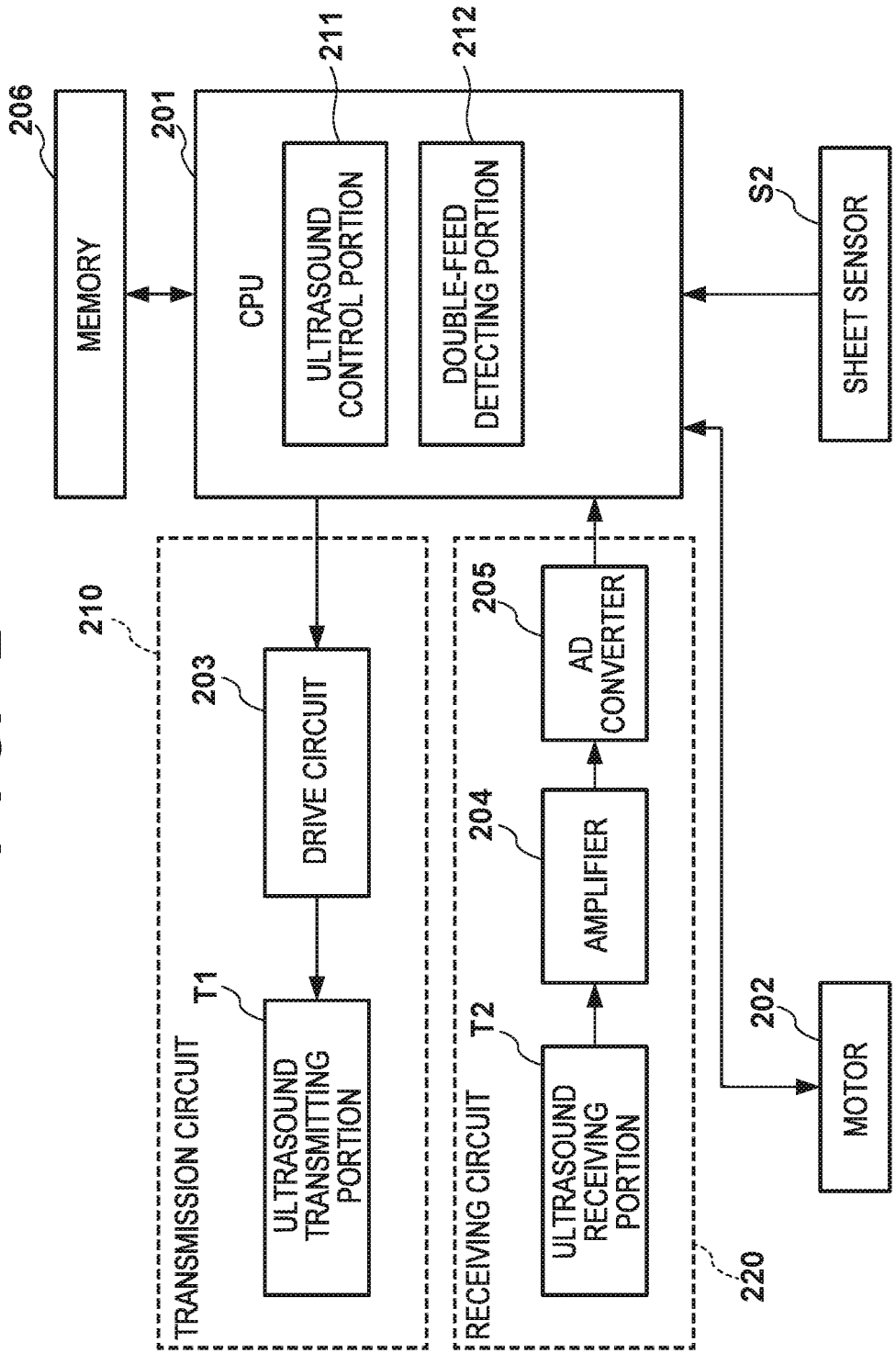
FIG. 2 is a block diagram of a controller.

As described using FIG. 2, the ultrasound receiving circuit 220 has the ultrasound receiving portion T2, the amplifier 204, and the AD converter 205. The ultrasound receiving portion T2 outputs the output signal corresponding to the amplitude of the ultrasound transmitted by the ultrasound transmitting portion T1. The amplifier 204 amplifies the output signal that has been output from the ultrasound receiving portion T2. The AD converter 205 performs analog-digital conversion on the output signal that has been amplified by the amplifier 204. In particular, the amplifier 204 amplifies the output signal from the ultrasound receiving portion T2 with a first degree of amplification when the threshold value is determined, and amplifies the output signal from the ultrasound receiving portion T2 with a second degree of amplification, which is larger than the first degree of amplification, when it is detected whether or not double-feed of a plurality of sheets has occurred. This configuration enables saturation of the amplitude of the output signal to be suppressed when determining the threshold value. Furthermore, when double-feed is detected, even if the ultrasound is dampened due to a sheet and the amplitude of the output signal from the ultrasound receiving portion T2 decreases, the output signal can be amplified to the degree that double-feed can be detected.

As described using FIG. 5, the amplifier 204 may have the inversion amplifying circuit 501, which serves as a first amplification stage, and the inversion amplifying circuit 502, which is connected to the first amplification stage as a subsequent stage of the first amplification stage and serves as a second amplification stage. The AD converter 205 may have the AD conversion circuit 503 serving as a first conversion circuit that performs analog-digital conversion on the output signal that has been amplified at the first amplification stage. The AD converter 205 may have the AD conversion circuit 504 serving as a second conversion circuit that performs analog-digital conversion on the output signal that has been amplified at the first amplification stage and also amplified at the second amplification stage. In this case, the double-feed detecting portion 212 determines the threshold value using the amplitude level of the output signal that has been output by the AD conversion circuit 503. With this configuration, the threshold value is determined using the amplitude level that is not saturated due to a small degree of amplification. The double-feed detecting portion 212 detects whether or not double-feed of a plurality of sheets has occurred, using the amplitude level of the output signal that has been output by the AD conversion circuit 504. This configuration enables double-feed to be detected even in the case of an amplitude level that has decreased due to the damping caused by a sheet.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-168139, filed Aug. 27, 2015 which is hereby incorporated by reference herein in its entirety.

What is claimed is:

1. A sheet conveyance apparatus comprising:
a conveyance unit configured to convey a sheet on a conveyance path;
a transmitter configured to transmit ultrasound to the conveyance path based on a burst wave;
a receiver configured to receive the ultrasound transmitted from the transmitter, the receiver being mounted opposing the transmitter;
a double-feed detector configured to detect whether or not double-feed of a plurality of sheets has occurred on the conveyance path by comparing, with a threshold value, an amplitude level of an output signal that is output from the receiver; and
an ultrasound controller configured to control generation of a plurality of burst waves so that in a process for determining the threshold value a plurality of burst waves are generated at a first interval to transmit a plurality of ultrasound from the transmitter, and in a process for detecting a double-feed of a plurality of sheets a plurality of burst waves are generated at a second interval shorter than the first interval to transmit a plurality of ultrasound from the transmitter;
wherein the double-feed detector determines the threshold value that enables distinction between double-feed and single-feed, based on an amplitude level of an output signal that has been output by the receiver receiving the ultrasound transmitted by the transmitter based on a plurality of burst waves generated at the first interval in a state where no sheet exists on the conveyance path.

2. The sheet conveyance apparatus according to claim 1, wherein the transmitter and the receiver are mounted relative to the conveyance path.

3. The sheet conveyance apparatus according to claim 1, wherein the first interval is a time required for an echo of the ultrasound transmitted from the transmitter to become smaller than or equal to a predetermined tolerance limit.

4. The sheet conveyance apparatus according to claim 1, wherein the second interval is a time required for an echo of the ultrasound transmitted from the transmitter to become smaller than or equal to a predetermined tolerance limit.

5. The sheet conveyance apparatus according to claim 1, wherein the double-feed detector determines the threshold value by multiplying the amplitude level obtained in a state where no sheet exists on the conveyance path by a correction coefficient.

6. The sheet conveyance apparatus according to claim 1, wherein the double-feed detector determines the threshold value by multiplying the amplitude level obtained in a state where no sheet exists on the conveyance path by a correction coefficient and a margin.

7. A sheet conveyance apparatus comprising:
a conveyance unit configured to convey a sheet on a conveyance path;
a transmitter configured to transmit ultrasound to the conveyance path;
a receiver configured to receive the ultrasound transmitted from the transmitter, the receiver being mounted opposing the transmitted;
a double-feed detector configured to detect whether or not double-feed of a plurality of sheets has occurred on the conveyance path by comparing, with a threshold value, an amplitude level of an output signal that is output from the receiver; and
an ultrasound controller configured to cause the transmitter to transmit ultrasound at a first burst interval when determining the threshold value, and cause the transmitter to transmit ultrasound at a second burst interval, which is shorter than the first burst interval, when detecting the double-feed of sheets,
wherein the double-feed detector determines the threshold value that enables distinction between double-feed and single-feed, based on an amplitude level of an output signal that has been output by the receiver receiving the ultrasound transmitted at the first burst interval by the transmitter in a state where no sheet exists on the conveyance path,
wherein the ultrasound controller causes the transmitter to transmit ultrasound in a state where no sheet exists on the conveyance path from a time when an instruction to convey a sheet is given until the sheet reaches a space between the transmitter and the receiver, and causes the double-feed detector to determine the threshold value, and
upon the sheet reaching the space between the transmitter and the receiver, the double-feed detector detects whether or not double-feed of a plurality of sheets has occurred, using the threshold value.

8. A sheet conveyance apparatus comprising:
a conveyance unit configured to convey a sheet on a conveyance path;
a transmitter configured to transmit ultrasound to the conveyance path;
a receiver configured to receive the ultrasound transmitted from the transmitter, the receiver being mounted opposing the transmitter;
a double-feed detector configured to detect whether or not double-feed of a plurality of sheets has occurred on the conveyance path by comparing, with a threshold value, an amplitude level of an output signal that is output from the receiver; and
an ultrasound controller configured to cause the transmitter to transmit ultrasound at a first burst interval when determining the threshold value, and cause the transmitter to transmit ultrasound at a second burst interval, which is shorter than the first burst interval, when detecting the double-feed of sheets,
wherein the double-feed detector determines the threshold value that enables distinction between double-feed and single-feed, based on an amplitude level of an output signal that has been output by the receiver receiving the ultrasound transmitted at the first burst interval by the transmitter in a state where no sheet exists on the conveyance path,
wherein the receiver includes:
a receiving element configured to output an output signal corresponding to an amplitude of the ultrasound received;
an amplifier configured to amplify the output signal that has been output from the receiving element; and
a convertor configured to perform analog-digital conversion on the output signal that has been amplified by the amplifier, wherein the amplifier amplifies the output signal from the receiving element with a first degree of amplification in a case where the threshold value is determined, and amplifies the output signal from the receiving element with a second degree of amplification, which is larger than the first degree of amplification, in a case where it is detected whether or not double-feed of a plurality of sheets has occurred.

9. The sheet conveyance apparatus according to claim 8, wherein the amplifier has a first amplification stage, and a second amplification stage connected to the first amplification stage as a subsequent stage of the first amplification stage,
wherein the convertor has a first conversion circuit configured to perform analog-digital conversion on the output signal that has been amplified at the first amplification stage, and a second conversion circuit configured to perform analog-digital conversion on the output signal that has been amplified at the first amplification stage and also amplified at the second amplification stage,
wherein the double-feed detector determines the threshold value using the amplitude level of the output signal that has been output by the first conversion circuit, and
wherein the double-feed detector detects whether or not double-feed of a plurality of sheets has occurred, using the amplitude level of the output signal that has been output by the second conversion circuit.

10. An image reading apparatus comprising:
a conveyance unit configured to convey a sheet on a conveyance path;
a transmitter configured to transmit ultrasound to the conveyance path based on a burst wave;
a receiver configured to receive the ultrasound transmitted from the transmitter, the receiver being mounted opposing the transmitter;
a double-feed detector configured to detect whether or not double-feed of a plurality of sheets has occurred on the conveyance path by comparing, with a threshold value, an amplitude level of an output signal that is output from receiver;
an ultrasound controller configured to control generation of a plurality of burst waves so that in a process for determining the threshold value a plurality of burst waves are generated at a first interval to transmit a plurality of ultrasound from the transmitter, and in a process for detecting a double-feed of a plurality of sheets a plurality of burst waves are generated at a second interval shorter than the first interval to transmit a plurality of ultrasound from the transmitter,
wherein the double-feed detector determines the threshold value that enables distinction between double-feed and single-feed, based on an amplitude level of an output signal that has been output by the receiver receiving the ultrasound transmitted by the transmitter based on a burst wave generated at the first interval in a state where no sheet exists on the conveyance path; and
a reader configured to read an image formed on the sheet if the double-feed detector does not detect double-feed.

11. The image reading apparatus according to claim 10, wherein the transmitter and the receiver are mounted relative to the conveyance path.

12. A method in a sheet conveyance apparatus, the method comprising:
transmitting, to a conveyance path, ultrasound at a first burst interval in a state where no sheet exists on the conveyance path based on a burst wave, by a transmitter;
receiving the ultrasound transmitted at the first burst interval by the transmitter in the state where no sheet exists on the conveyance path, by a receiver mounted opposing the transmitter;
determining a threshold value that enables distinction between double-feed and single-feed, based on an amplitude level of an output signal that has been output by the receiver receiving the ultrasound transmitted by the transmitter based on a plurality of burst waves generated at a first interval in the state where no sheet exists on the conveyance path;
conveying a sheet on the conveyance path, by a conveyor;
transmitting ultrasound based on a plurality of burst waves generated at a second interval shorter than the first interval in a state where a sheet exists on the conveyance path, by the transmitter;
receiving ultrasound that has been transmitted at the second burst interval by the transmitter and penetrated the sheet, by the receiver; and
detecting whether or not double-feed of a plurality of sheets has occurred on the conveyance path by comparing, with the threshold value, the amplitude level of the output signal output from the receiver that has received the ultrasound which has penetrated through the sheet.

* * * * *